(12) United States Patent
Loock et al.

(10) Patent No.: US 6,842,548 B2
(45) Date of Patent: Jan. 11, 2005

(54) OPTICAL LOOP RING-DOWN

(75) Inventors: Hans-Peter Loock, Kingston (CA); R. Stephen Brown, Kingston (CA); Igor Kozin, Kingston (CA); Zhaoguo Tong, Kingston (CA); Richard D. Oleschuk, Kingston (CA)

(73) Assignee: Queen's University at Kingston, Kingston (CA)

(*) Notice: Subject to any disclaimer, the term of this patent is extended or adjusted under 35 U.S.C. 154(b) by 211 days.

(21) Appl. No.: 10/156,238

(22) Filed: May 29, 2002

(65) Prior Publication Data

US 2003/0007715 A1 Jan. 9, 2003

Related U.S. Application Data

(60) Provisional application No. 60/331,181, filed on Nov. 9, 2001, and provisional application No. 60/293,518, filed on May 29, 2001.

(51) Int. Cl.[7] ................................................ G02B 6/26
(52) U.S. Cl. .......................................... 385/15; 385/12
(58) Field of Search ............................... 385/12, 13, 15

(56) References Cited

U.S. PATENT DOCUMENTS

| | | | | |
|---|---|---|---|---|
| 4,530,603 A | * | 7/1985 | Shaw et al. | 356/480 |
| 4,812,645 A | * | 3/1989 | Griffiths | 250/227.14 |
| 4,930,852 A | * | 6/1990 | Wheeler et al. | 359/315 |
| 5,187,983 A | * | 2/1993 | Bock et al. | 73/705 |
| 6,396,856 B1 | * | 5/2002 | Sucha et al. | 372/25 |
| 6,544,393 B1 | * | 4/2003 | Kunnecke | 204/409 |

OTHER PUBLICATIONS

Atherton, K., et al., "Fibre optic intra cavity spectroscopy––combined ring down and ICLAS architectures using fibre lasers," *SPIE* 4204:124–130 (2001).

Pipino, A.C.R., et al., "Evanescent wave cavity ring–down spectroscopy with a total–internal–reflection minicavity," *Rev. Sci. Instrum.* 68:2978–2989 (1997).

Pipino, A.C.R., et al., "Evanescent wave cavity ring–down spectroscopy for probing surface processes." *Chem. Phys. Letts.* 280:104–112 (1997).

Pipino, A.C.R., "Evanescent wave cavity ring–down spectroscopy for ultra–sensitive chemical detection," *SPIE* 3535:57–63 (1998).

Stewart G., et al., "Intra–cavity and ring–down cavity absorption with fibre amplifiers for trace gas detection," *SPIE* 4185:448–451 (2000).

Stewart, G., et al., "An investigation of an optical fibre amplifier loop for intra–cavity and ring–down cavity loss measurements," *Meas. Sci. Technol.* 12:843–849 (2001).

Von Lerber, T., et al., "Time constant extraction from noisy cavity ring–down signals," *Chem. Phys. Letts.* 353:131–137 (2002).

* cited by examiner

*Primary Examiner*—Ellen E. Kim
(74) *Attorney, Agent, or Firm*—Stephen J. Scribner; Carol Miernicki Steeg

(57) ABSTRACT

The invention provides a method and apparatus for measuring one or more optical properties of a test medium, comprising providing an optical waveguide loop comprising a test medium, illuminating the optical waveguide loop with a plurality of light pulses, and detecting roundtrips of the light pulses at one or more locations along the loop, wherein the detected light pulses are indicative of one or more optical properties of the test medium. Preferably, ring-down time of said light pulses is determined. The invention provides measures of optical properties such as absorbance and refractive index of a test medium such as a gas, a liquid, and a solid material.

50 Claims, 11 Drawing Sheets

OPTICAL LOOP RING-DOWN

RELATED APPLICATIONS

This application claims the benefit of the filing date of U.S. Provisional Patent Application No. 60/331,181, filed on Nov. 9, 2001, and of U.S. Provisional Patent Application No. 60/293,518, filed on May 29, 2001, the disclosures of which are incorporated herein by reference in their entirety.

FIELD OF THE INVENTION

This invention relates to methods and apparatus for measuring optical characteristics of a test medium or media. In particular, the invention relates to use of ring-down time of light in an optical loop to measure optical characteristics of a test medium or media.

BACKGROUND OF THE INVENTION

Measurement of low optical losses in an absorbing medium is commonly performed by applying a light signal to a long absorbance path length, using single-pass or multi-pass paths in the absorbing medium. The signal is measured as a function of the desired parameter, such as wavelength of the light, time, concentration, etc., by a light detector, in comparison with a reference channel. Such a light detector normally terminates the light path of the signal and the reference channel. These measurements require either light sources with very low variations in intensity or a good reference scheme. In particular, the sensitivity of the single or multipass absorption techniques is limited by the pathlengths that can be achieved, the sensitivity of the detector towards small changes in transmission, and the temporal and spatial stability of the signal, which in turn is influenced by the temporal and spatial stability of the light source and of the reference vs. signal channel, the alignment of the source, the medium and detector, and of the detector and associated equipment. As a result, measurement of low optical losses using such technique is difficult and yields unreliable data.

The use of ring-down time of a light signal in a cavity consisting of mirrors can also be used to measure optical characteristics of an absorbing medium. Such optical cavities consist of two or more mirrors, between which an optical signal is reflected to characterize the mirrors as well as the optical characteristics of an absorbing medium (e.g., gases, molecular beams, etc.) between the mirrors (Romanini et al. 1993; Scherer et al. 1997; Berden et al. 2000; Lehmann, U.S. Pat. No. 5,528,040, issued Jun. 18, 1996).

A ring-down cavity has been set up with a crystal inside a cavity defined by mirrors, and the spectra of compounds at the surface of the crystal have been measured using evanescent wave spectroscopy (Pipino et al. 1997). Also, the crystal faces have been used to define a cavity and thereby create a cavity without mirrors, wherein the signal rings down due to internal reflection of the crystal. This technique has also been used for evanescent wave spectroscopy (Pipino, U.S. Pat. No. 5,835,231, issued Nov. 10, 1998).

Although cavity ring-down spectroscopy (CRDS) is well established as a gas phase method, applications in condensed phase have, until recently, been limited to absorption measurements of films through evanescent field experiments on the surface of all-solid state cavities (Pipino et al. 1997) and to films deposited on windows inside the cavity (Engeln et al. 1999).

Very recently CRDS was shown to be applicable to absorption measurements on liquid samples, in which a high finesse cavity was either filled entirely with a liquid sample (Hallock et al. 2002) or the liquid was contained in cuvettes (Xu et al. 2002). To our knowledge, there have only been two previous attempts at ring-down measurements using optical fibers. Von Lerber et al. (2002) constructed a cavity by depositing highly reflective coatings onto both fiber end facets of a 10 m optical fiber. Stewart et al. (2001) inserted a gas phase absorption cell into a fiber-loop, leading to very high transmission losses. These losses necessitated the use of a fiber amplifier, and the sensitivity of measurements using such an active loop depended strongly on the amplifier's temporal stability.

SUMMARY OF THE INVENTION

According to one aspect of the invention there is provided a method for measuring one or more optical properties of a test medium, comprising: providing an optical waveguide loop comprising a test medium; illuminating the optical waveguide loop with a plurality of light pulses; and detecting roundtrips of said light pulses at one or more locations along the loop; wherein said detected light pulses are indicative of one or more optical properties of the test medium.

Preferably, the method further comprises determining ring-down time of said light pulses. Also preferably, the optical waveguide loop is passive.

In one embodiment, a period between light pulses is greater than the ring-down time of a light pulse. In such embodiment, the ring-down time may be determined by summing the roundtrips for light pulses at each instance in time. In another embodiment, the method further comprises providing light pulses of smaller pulse width and/or a longer waveguide loop, such that roundtrips from each light pulse are separated in time. In a further embodiment, the method further comprises providing light pulses of greater pulse width and/or a shorter waveguide loop, such that an envelope of the ring-down time is measured.

In another embodiment, a period between light pulses is less than the ring-down time of a light pulse. In such embodiment, the ring-down time may be determined from an integrated waveform corresponding to the sum of ring-down waveforms for the light pulses. In a further embodiment, the method comprises providing light pulses of smaller pulse width and/or a longer waveguide loop, such that roundtrips from each light pulse are separated in time. In yet another embodiment, the method comprises providing light pulses of greater pulse width and/or a shorter waveguide loop, such that an envelope of the ring-down is measured.

In various embodiments, the optical waveguide may be an optical fiber, which may further comprise a fiber optic splice connector, or a fusion spliced connection. In some embodiments, the waveguide loop is the test medium.

In one embodiment, the test medium is exposed to light that is guided in by the optical waveguide loop using a capillary flow channel. In another embodiment, the test medium is in the vicinity of the optical waveguide and is exposed an evanescent wave of light that is guided by the optical waveguide loop.

In various embodiments of the method, the optical property may be absorbance, refractive index, or evanescent wave spectrum. The light pulses have at least one wavelength selected from infra-red (IR), visible, and ultra-violet. The number of light pulses may be between about 10 and 10,000, preferably about 200 to 8,000. The test medium is selected from a gas, a liquid, and a solid material.

In a preferred embodiment, the invention provides a method for measuring one or more optical properties of a test medium, comprising: providing an optical waveguide loop comprising a test medium; and measuring ring-down time of a plurality of light pulses travelling around the loop and through the test medium; wherein the ring-down time is indicative of one or more optical properties of the test medium.

According to another aspect of the invention there is provided an apparatus for measuring one or more optical properties of a test medium, comprising: an optical waveguide loop comprising a test medium; a light source for illuminating the loop with a plurality of light pulses; and a detector for detecting roundtrips of said light pulses at one or more locations along the loop; wherein said detected light pulses are indicative of one or more optical properties of the test medium.

In one embodiment, the apparatus further comprises a device for displaying and/or storing and/or manipulating data corresponding to light pulses. In a preferred embodiment, ring-down time of said light pulses is determined. Preferably, the optical waveguide loop is a passive loop.

In one embodiment, a period between light pulses is greater than the ring-down time of a light pulse. In such embodiment, the ring-down time may be determined by summing the roundtrips for light pulses at each instance in time. In another embodiment of the apparatus, there is provided light pulses of smaller pulse width and/or a longer waveguide loop, such that roundtrips from each light pulse are separated in time. In a further embodiment of the apparatus, there is provided light pulses of greater pulse width and/or a shorter waveguide loop, such that an envelope of the ring-down time is determined.

In another embodiment, a period between light pulses is less than the ring-down time of a light pulse. In such embodiment, the ring-down time may be determined from an integrated waveform corresponding to the sum of ring-down waveforms for the light pulses. In a further embodiment, there is provided light pulses of smaller pulse width and/or a longer waveguide loop, such that roundtrips from each light pulse are separated in time. In yet another embodiment, there is provided light pulses of greater pulse width and/or a shorter waveguide loop, such that an envelope of the ring-down is measured.

In various embodiments, the optical waveguide is an optical fiber, which may further comprise a fiber optic splice connector, or a fusion spliced connection. In some embodiments, the waveguide loop is the test medium.

In one embodiment, the test medium is exposed to light that is guided in by the optical waveguide loop using a capillary flow channel. In another embodiment, the test medium is in the vicinity of the optical waveguide and is exposed an evanescent wave of light that is guided by the optical waveguide loop.

In various embodiments, the optical property may be absorbance, refractive index, or evanescent wave spectrum. The light pulses have at least one wavelength selected from infra-red (IR), visible, and ultra-violet. The number of light pulses may be between about 10 and 10,000, preferably about 200 to 8,000. The test medium may be selected from a gas, a liquid, and a solid material.

In yet a further embodiment, the optical property is absorbance and the apparatus further comprises a microfluidic device.

According to a preferred embodiment of the invention there is provided an apparatus for measuring one or more optical properties of a test medium, comprising: an optical waveguide loop comprising a test medium; a light source for illuminating the loop with a plurality of light pulses; a detector for detecting roundtrips of said light pulses at one or more locations along the loop; and a device for displaying and/or storing and/or manipulating data corresponding to light pulses; wherein ring-down time of said light pulses is determined; and wherein said ring-down time is indicative of one or more optical properties of the test medium. In accordance with a preferred embodiment, the optical waveguide loop is passive.

BRIEF DESCRIPTION OF THE DRAWINGS

Embodiments of the invention are described below, by way of example, with reference to the accompanying drawings, wherein.

DETAILED DESCRIPTION OF THE INVENTION

Figure 1:
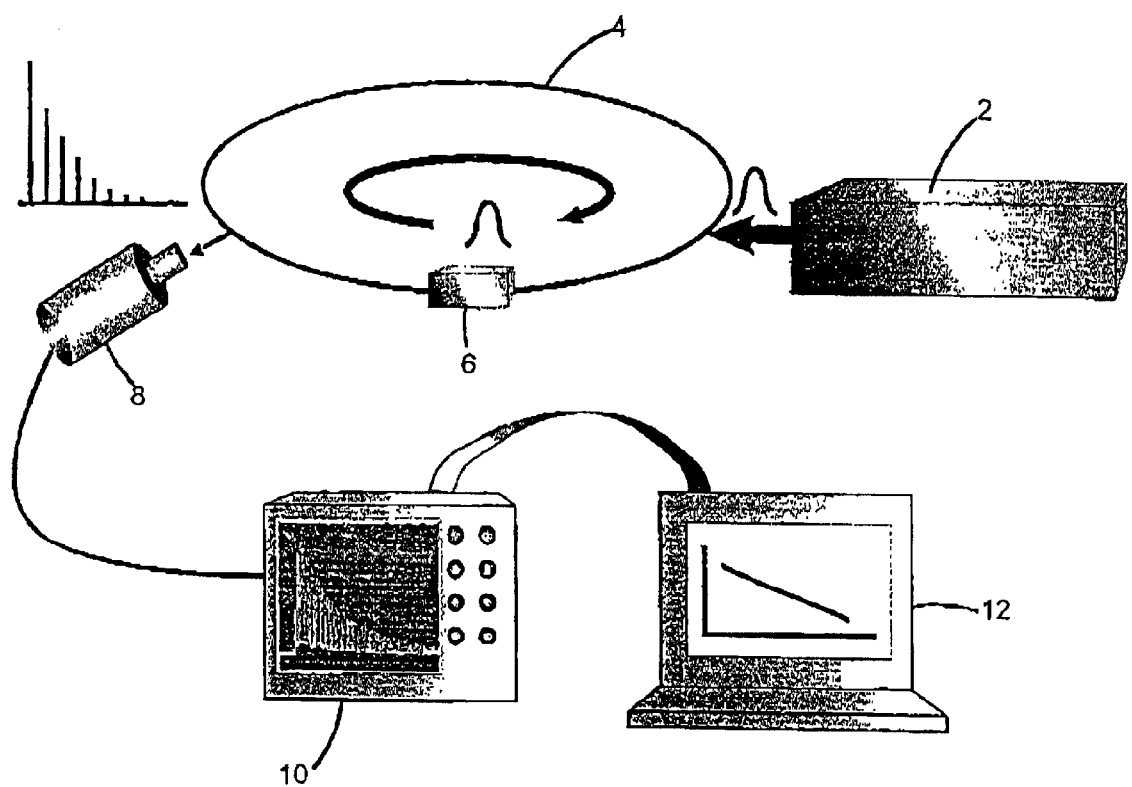
FIG. 1 is a block diagram of a fiber loop ring-down system for measuring optical properties of an optical fiber and connector.

According to a broad aspect of the invention, there is provided a method of measuring one or more optical properties of a test medium by measuring the ring-down time of a light pulse traveling around an optical waveguide loop and through the test medium. The invention provides a method by which the ring-down time of a light pulse in a waveguide loop can be used as an observable in characterizing the optical properties of a test medium.

As used herein, the term "test medium" is intended to mean any medium or material the optical properties of which can be measured in accordance with the invention. The test medium is exposed to at least a portion of the light that is guided by the optical waveguide, wherein that portion of light is either within the waveguide, or outside of the waveguide (i.e., the evanescent wave). Examples of test media include, but are not limited to, the optical waveguide loop itself, a portion of a second optical waveguide inserted into the loop, an optical connector or device, a sample of a gas, liquid, or solid material (e.g., a film or coating, such as a solid or liquid film deposited on the facet end of an optical fiber), or a stationary test medium. Gases and liquids can be introduced into the loop using, for example, a flow channel, a capillary, a capillary channel, and the like, which intersects the loop. A test medium can also be introduced to the optical waveguide loop outside of, but in the vicinity of the waveguide, so as to intercept at least a portion of the evanescent wave. For example, in the case where an optical fiber is used for the optical waveguide, a portion of the fiber cladding can be removed to expose a test medium to the evanescent wave in the vicinity of the fiber.

As used herein, the term "optical properties" is intended to mean any property of a medium that is light-dependent. Examples of optical properties are absorbance, refractive index, evanescent wave spectrum, and optical loss. Optical properties are indicative of, or related to, physical characteristics of a medium (e.g., density, structure (such as 1-, 2-, or 3-dimensional structure)). Thus, in accordance with the invention, one or more optical properties of a medium is/are indicative of one or more physical characteristics of the medium.

As used herein, the term "ring-down time" is intended to mean the time required for the intensity of a light pulse travelling in an optical waveguide loop to decrease to 1/e of its initial intensity. Each complete roundtrip of a light pulse corresponds to the light pulse passing a given location along the loop, and is sometimes also referred to as a "ring".

As used herein, the term "optical waveguide" is intended to encompass any conduit for light. An optical waveguide according to the invention is capable of being formed into or provided as a continuous loop, e.g., by joining the two ends of the waveguide together, such that a light pulse launched in the waveguide travels around the loop repeatedly. Examples of optical waveguides are optical fibers, such as those having a solid core, hollow core (i.e., capillary fiber), or liquid core, and waveguides based on high refractive index fluids. Optical waveguide can also be prepared on a substrate such as glass or polymeric material, for example, in embodiments where the invention comprises a microchip. Where optical fiber is employed, such fiber may be selected from commercially available fibers, including multi-mode and single mode fibers. The two ends of waveguides such as optical fibers are joined using splice connectors, such as any commercially available connector, fusion spliced connections, or any other suitable technique known in the art. Preferably, such fibers and connections have low absorbance. In this regard, waveguides based on high refractive index fluids are advantageous in that such connectors are not required.

An optical waveguide loop according to the invention is preferably as short as possible, to maximize the number of roundtrips a light pulse will complete before its intensity falls below the detectable threshold. In theory, there is no limit to the minimum length of the loop, and it is expected that for certain applications an entire apparatus employing optical loop ring-down can be fabricated on a microchip. However, in practice, the minimum length of the loop can be limited by factors that contribute to loss of the light pulse, such as a small radius of the bend in the waveguide (loss increases as radius decreases), high loss of a waveguide splice (e.g., a fiber optic splice connector), or, in the case where the loop is employed in an absorbance detector (see below), high loss in the sample channel. In cases where such losses are high, a longer loop is preferred. For fiber optic loops, practically the loop length is that which results in a radius of no less than about 3 cm (a loop length of about 20 cm). The maximum loop length is limited by that which is practical, with consideration given to the loss of the waveguide and the minimum number of passes of a light pulse required for a given measurement (e.g., 100). For fiber optic loops, a practical maximum length is about 100 m; however, the invention is not limited thereto.

It should be noted that in forming the loop, the optical waveguide can be "wound" into any shape, as may be required for compactness, etc., of the loop. This is of relevance when long loops are required. In particular, when a very long loop is used, but the number of roundtrips of a light pulse around the loop is low, the loop can be wound in such a configuration so as to allow the launching and/or detection of a light pulse simultaneously at two or more locations along the loop, such that multiple roundtrips within the loop are set up and/or detected.

It is preferred that the optical waveguide loop is a passive loop. As used herein, the term "passive loop" refers to a loop that does not have a device (e.g., an amplifier) for amplifying light.

In accordance with the invention, a light pulse can be of any wavelength from about 1500 nm (i.e., infra-red, IR) to about 200 nm (i.e., ultraviolet, UV). Use of UV can be problematic because of the degradative effects of UV light on optical materials, and comparatively high losses (e.g., 1% per m of optical fiber). However, UV is of particular interest in chemical, biochemical, biological, and environmental studies, because many compounds and substances of interest absorb in this wavelength. In some embodiments of the invention the light pulse has a narrow bandwidth (e.g., comprised of a single colour of light), whereas in other embodiments, the light pulse is wide band (e.g., white light). Suitable light sources are those light sources capable of producing a pulse of light having a pulse width at least about 20× less than the ring-down time, such as lasers. In embodiments employing a spectroscopic approach wherein ring-down time as a function of wavelength is sought, a tunable laser can be employed, and such laser "swept" to produce pulses over a range of wavelengths. The intensity of the light pulse should be high enough so as to complete a sufficient number of passes around the loop prior to degrading below the detectable threshold, but low enough to avoid damaging the optical waveguide. A light pulse can be coupled into the waveguide using any conventional means, such as a directional coupler. However, in the case of optical fiber, a light pulse can be coupled into the fiber simply by illuminating the fiber. Further, sufficient coupling can often be achieved without removing the jacket/cladding, although this will depend on the properties of the jacket/cladding used. Such coupling advantageously avoids the use of couplers, which have inherent loss. It can be shown that an increase in coupling efficiency can be achieved by adjusting the angle that the illuminating radiation forms with the waveguide as well as by adjusting the angle formed by polarization of the linearly polarized light beam with the waveguide. Further increases can be achieved by "funneling" the illuminating radiation into the fiber. The coupling efficiency that can be achieved is typically between $10^{-8}$ to $10^{-5}$.

Figure 2:
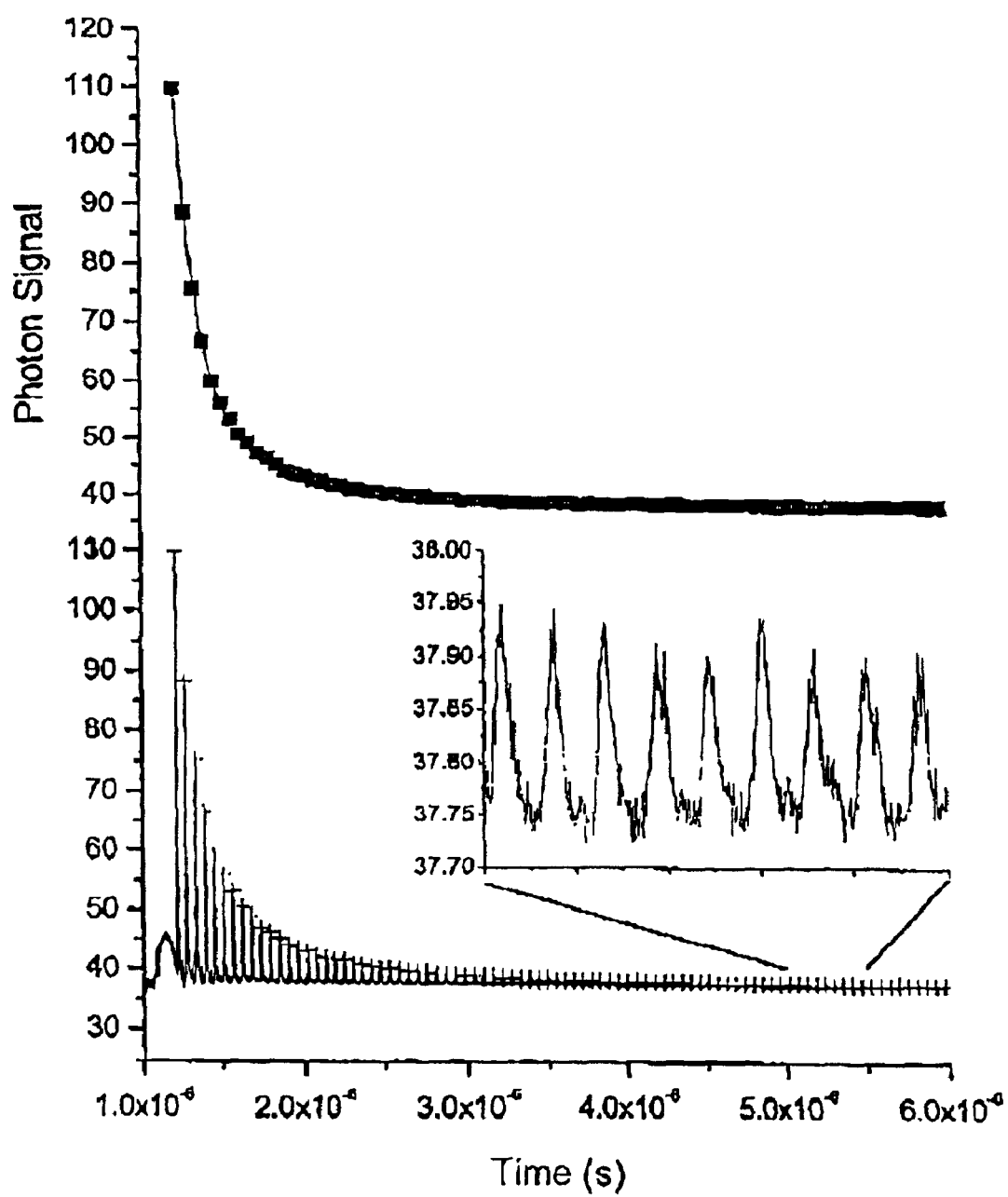
FIG. 2 shows a ring-down trace for a 12 m optical fiber. The upper panel shows a bi-exponential fit to the peak areas of the lower trace.

In one embodiment, shown in FIG. 1, a light pulse from a source such as a laser 2 is coupled into an optical wave guide, in this case an optical fiber 4, which is formed into a loop using a fiber splice connector 6. The light pulse traveling through the fiber loop is detected using a photon detector 8. The detected pulse is displayed on a suitable device such as an oscilloscope 10 and the data stored and analyzed in a computer 12. Once the light pulse is coupled into the fiber it experiences very little loss and it completes many trips around the loop before its intensity falls below a detection threshold. By measuring the decibel (dB) loss per pass and the ring-down time (see FIG. 2), various loss mechanisms of the light pulses can be characterized. According to the invention, such losses can be measured independently of power fluctuations of the light source. Thus, unlike conventional single or multipass-type devices, the invention is not sensitive to the intensity of the input light signal, to the input coupling efficiency of the light signal, or to drift of the light signal power with time or wavelength.

In a preferred embodiment of the method of the invention, the method comprises launching a single light pulse into the loop (i.e., a laser shot), recording the roundtrips of that shot, and then repeating this process a number of times (e.g., about 10 to 10,000 times, preferably about 200 to 8,000 times). Using more shots or pulses provides a more accurate measure of the ring-down time. According to this embodiment, the period between pulses is greater than the ring-down time. In such method, summing individual roundtrips at each instance on the time axis yields a plot of ring-down time like that shown in FIG. 2. However, in an alternative embodiment of the method of the invention, the period between light pulses can be less than the ring-down time. Such an alternative embodiment yields an integrated waveform that contains the sum of ring-down traces, and analysis (e.g., Fourier transform, exponential fitting) yields the ring-down time.

The embodiment shown in FIG. 1 is suitable for applications such as characterizing loss processes in fiber optic transmission. For example, the method can be used to accurately determine the absolute transmission spectrum of an optical fiber and of the fiber connector, as well as other optical properties such as refractive index, evanescent wave spectrum, and optical loss. Further, the effect of factors such as stress on the fiber can be evaluated with respect to such fiber properties.

In some embodiments (e.g., see Example 1, below), the length of the waveguide loop is chosen such that signals obtained from the photo detector from each roundtrip of a light pulse are well-separated. In an alternative embodiment, a light pulse of greater pulse width and/or shorter waveguide loop are used, and the envelope of the ring-down signal measured, as opposed to the integral of the individual roundtrip signals. This latter embodiment improves the quality of the fit to the curve of the ring-down time since the exponential decay is described by a larger number of points. In these embodiments, the period between pulses can be greater than, equal to, or less than the ring-down time. We note that in contrast to most other absorption measurement techniques, the number of data points available for extraction of the absorption signal is in fact larger for weak absorption processes than for strong absorption processes. Therefore, the method of the invention is well suited to weak absorbers and/or short absorption pathlengths.

As used herein, the term "pulse width" is intended to mean the temporal full-width half-maximum of the light pulse.

In one embodiment, the invention is used to measure one or more optical properties of a non-gaseous test medium, using a short optical path length through the test medium (e.g., a path length less than about 100 $\mu$m, preferably about 1 to 10 $\mu$m). It will be appreciated that this embodiment requires only very small volumes of test medium (e.g., in the order of picoliters).

In a further embodiment of the invention the laser source is replaced with a fast LED, and the loop is a fiber loop in which light pulses can be launched simultaneously and detected simultaneously at multiple locations of the loop (e.g., by wrapping the fiber around a cylinder so as to form many loops). The resulting ring-down signal does not carry a signature of separate pulses, but consists of a smooth exponential decay.

Light pulses traveling through fiber loops have been employed in fiber gyros and Sagnacs to measure phase and amplitude shifts as a function of external parameters (e.g., angular velocity of the fiber gyro) (*Optical Fibers Sensors: Systems and Applications* 1989). In accordance with the invention, pulses can be launched in both clockwise and counterclockwise directions around the loop, to create an interference pattern that is spatially confined in the case of short pulses. It is expected that this interference pattern can be used to extract information concerning, for example, the speed of light in the fiber (i.e., angular velocity of the loop).

A common use for fiber loops is as all-optical storage or buffer media for pulse trains in the telecommunications industry. The length of the pulse train (the amount of information) that may be stored is determined by the length of the fiber (Langenhorst et al. 1996). Usually the pulse train is amplified with each pass and it has been shown that using a semiconductor laser amplifier in a loop mirror (SLALOM) configuration a 30 ps pulse can be forced to undertake $10^6$ passes in a loop of 1,000 m with out significant degrading (Eiselt et al. 1993). Other workers demonstrated reliable storage of a 12 data bit pulse train for up to 30 minutes in a optical fiber loop using a vertical to surface transmission electro-photonic device (Yamanaka et al. 1993). Clearly, when the fiber loop is used as an all-optical storage device amplification of the roundtrips after a given number of passes is required. Indeed, as demonstrated herein (see Example 1, below), information contained in a pulse or pulse train can be stored in a passive fiber optic loop only for up to 5 $\mu$s without amplification.

The optical loop ring-down method of the invention provides for an extremely sensitive absorption spectroscopic technique, and as such it is suitable for numerous applications, as exemplified by the embodiments described below.

Figure 3:
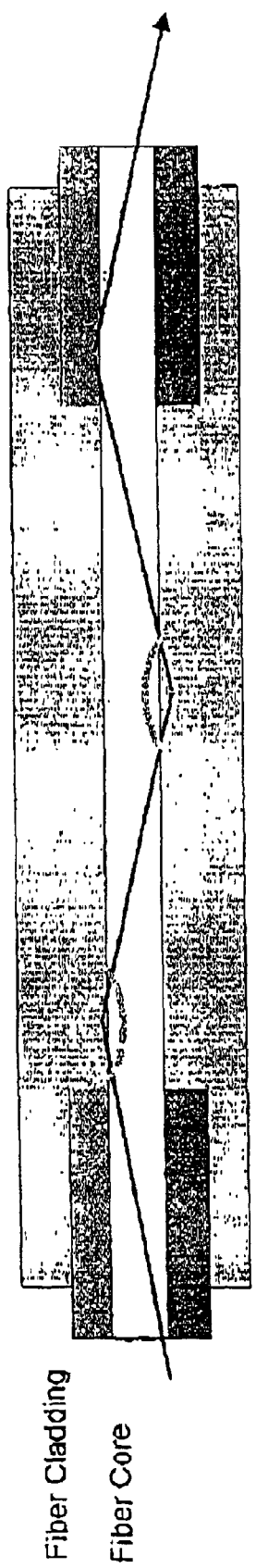
FIG. 3 is a schematic diagram showing evanescent wave spectroscopy.

In one embodiment, the optical loop ring-down method is used to detect the presence of one or more compounds, or to measure the absorption spectrum of one or more compounds, by evanescent wave spectroscopy. In such embodiment, the fiber cladding on a section of the loop can either be removed, or replaced with a chemically modified polymer, such as a silicon-based polymer, to permit detection and recording of the evanescent wave absorption spectrum produced by a compound(s) in the vicinity of the fiber core. A suitable modified polymer is one into which the compound of interest will partition. This is shown schematically in FIG. 3, where the polymer absorbs light each time the light pulse is reflected within the fiber. Such increase in absorbance corresponds to a decrease in ring-down time. Evanescent wave spectroscopy using ring-down phenomena has been demonstrated by Pipino and Hudgens, who used the ring-down of a laser pulse coupled into a quartz crystal to record the evanescent spectra of compounds absorbed on the crystal faces (Pipino et al. 1997; Pipino, U.S. Pat. No. 5,986,768, issued Nov. 16, 1999; Pipino, U.S. Pat. No. 5,835,231, issued Nov. 10, 1998). However, the loop ring-down method of the invention is less sensitive to laser alignment, and a long loop can be provided to allow for spatially separate illumination and detection regions.

In yet another embodiment, there is provided a method of measuring polarization-dependent loss using pulsed polarized laser light as a source and a polarization-maintaining fiber as a medium for the loop. Polarization-dependent loss is an important quantity in the telecommunications industry; however, such measurements are difficult to undertake with currently available technology.

According to another aspect of the invention there is provided an apparatus for measuring one or more optical properties of a test medium by measuring the ring-down time of a light pulse traveling around an optical waveguide loop and through the test medium. An example of such an apparatus is an absorbance detector.

In accordance with this aspect of the invention, the loop is interrupted by inserting a test medium therein. The test medium is a material for which optical properties are to be measured. For example, where optical fiber is employed, the medium used for index matching in the fiber-splice can be replaced with a test medium such as water, organic solvents, etc. Typically, such test medium will have a refractive index different from the refractive index of the fiber core. In such an embodiment, the space between the two fiber ends acts as a Fabry-Perot cavity. The loss processes are then determined by the refractive index of this cavity with respect to the fiber as well as by the modes present in the fiber. It is therefore necessary to accurately determine the mode structure of the Fabry-Perot cavity and its change as a function of the refractive index of the cavity medium. Maintaining a stable mode structure in a conventional cavity ring-down laser absorption spectroscopy experiment is challenging, since the mirrors are typically spaced by tens of centimeters and the laser pulse coupled into the cavity contains a large number of modes. In this embodiment, however, the loop substantially simplifies the measurement of the cavity modes if a single mode waveguide is used.

In one embodiment, the invention provides an absorption detector wherein a test medium for absorption measurement is introduced into the optical path of the optical loop. This can be accomplished by providing the sample material in, for example, a capillary or a flow channel, appropriately interfaced with the optical loop. For example, depending on the dimensions of the optical waveguide and the capillary, flow channel, or the like, the latter can either sever the optical waveguide, or it can pass through the waveguide, via, for example, a hole bored in the waveguide. Further, at least a portion of the optical waveguide loop can be incorporated into a chip, such as, for example, a microfluidic device (see Example 2, below). For example, where optical fiber is employed, the splice connector can be replaced with such a microfluidic device (e.g., a "lab-on-a-chip" device). Such devices are provided with channels having cross-sections in the order of microns, for carrying small amounts of analyte solution. The solutions can be accurately separated into their solutes in the channels. A microfluidic device thus provides a well-defined small gap between the waveguide ends, for which the mode structure can be accurately determined. The waveguide loop intersects one such channel, thereby forming part of a sensitive, selective absorption detector. The detection limit is estimated to be about $\epsilon$[l/mol m]*c[mol/l]=100 m$^{-1}$. A strongly absorbing molecule (e.g., $\epsilon$=10$^6$ l/mol m) can therefore be detected at sub millimolar concentrations. This estimate is based on a base loss of about 2% per pass in the channel and an absorption loss of 0.001 m$^{-1}$ of a fiber optic waveguide. Improvement of the detection limit can be achieved through a number of means, for example, by using a lower base loss fiber connector and a low loss fiber, by simultaneously illuminating many locations on the loop (e.g., using a cylindrical lens and a fiber which is wrapped around a cylindrical support), and by using a higher repetition rate of the light source (e.g., laser). In consideration of the latter point, it is noted that to resolve the roundtrips and analyze ring-down time as described above, the maximum pulse repetition rate is limited by the ring-down time and is about 200 kHz. Given that about 100 to 10,000 laser shots are required for an accurate measurement, the time resolution of such an absorption detector would be limited to about 500 $\mu$s to 50 ms. When using higher repetition rates the roundtrips start overlapping. Ring-down information is then contained in a composite wave form and is most easily extracted using a Fourier transform frequency analysis.

In a variation of this embodiment, polarization-maintaining fibers and optically active analytes are used, such that small quantities of absorbing media can be detected in a small absorption cell.

The contents of all cited references are incorporated herein by reference in their entirety.

The invention is further described by way of the following non-limiting examples.

WORKING EXAMPLES

Example 1

Fiber Loop Ring-Down Spectroscopy

Introduction

The characterization of optical properties, such as transmission spectrum or typical dB loss per unit length, of optical fibers is of central importance to any industry that uses or manufactures these fibers. Frequently, these properties are determined using a long length of fiber and measuring, e.g., the transmission spectrum, using a well calibrated and stable light source and detector. Measuring the optical properties and typical losses of fiber connections (fusion splices or mechanical splices) is more difficult since an individual splice ideally does not contribute much to the overall loss and therefore the measurement will frequently only give an upper limit for the loss. Alternatively, one can determine the average loss of a connection using are large number of splices, but will not be able to characterize the distribution of losses of those connections easily.

The fiber loop ring-down technique of the invention can be used to characterize the optical properties of optical fibers. Moreover the fiber loop ring-down technique is a substantial improvement over previously employed techniques, in that it is independent of shot-to-shot variations in the laser light intensity. The fiber-loop ring-down technique has the added advantage that it is suitable for recording absorption spectra of solid and liquid samples.

In the setup described below, a length of optical fiber is wound into a loop using a mechanical fiber splice connector. Pulsed laser light is coupled directly into the fiber. Light pulses are trapped inside the core of the fiber and complete many passes around the loop before loss processes such as self-absorption of the fiber and of the connector diminish the pulse intensity below the detection threshold. The intensity of light pulses travelling around the loop is determined using a fast photon detector placed near a bend in the optical fiber.

For each laser pulse a sequence of exponentially decaying ring-down pulses ("roundtrips") is observed. Their intensity follows the equation:

$$\frac{dI}{dt} = -I[(1-T_{splice}) + A]c/L$$

where $T_{splice}$ is the transmissivity of the connector, L is its length of the fiber loop and c is the speed of light in the fiber core. The absorption of the fiber core $A=-\epsilon x$ simply adds to the fiber loss.

Integration leads to the roundtrip intensity, $I_n$, after n roundtrips $$I_n = I_0 T^n e^{-n\epsilon L}$$

The loss $$\Gamma = 1 - e^{-1/\tau}$$

can then be described by the 1/e ring-down time $$\tau = \frac{L}{c[\epsilon L - \ln T_{splice}]}$$

This ring-down time characterizes a single exponential decay of the amplitude of the roundtrips and depends on the loss in the connector and inside the fiber. As is apparent from the above equation, in the calculation of the transmissivity one will have to distinguish between losses that occur once per roundtrip and processes that occur continuously.

The capabilities of the method of the invention are illustrated below by measuring the absorption spectra of two different optical fibers and of a commercial fiber splice connector.

Experiment

The experimental setup is shown in FIG. 1. As a light source we used a tunable dye laser (525 to 550 nm, 780 to 850 nm) pumped by nitrogen laser, with a bandwidth of about 2 nm, a pulsewidth of 600 ps and a power of 20 µJ. The output of this laser is coupled into the optical fiber loop (length 2 to 77 m) at a r=4 cm bend of the fiber. Two different multimode optical fibers were used at different regions of the visible spectrum (Anhydroguide G (Low OH Vis-IR), for 800 to 850 nm measurements; Superguide G (UV-Vis), for 500 to 550 nm measurements; both from Fiberguide Industries, N.J.). A photomultiplier tube (PMT) (Hamamatsu R955) was located at some distance (min. 50 cm) away from the excitation region and monitored the emitted light at a similar r=3 cm bend of the fiber. The PMT was gated such that the first 40 ns after each laser pulse were not recorded. This proved necessary since the photon signal had abnormally high intensity—likely from stray light and light coupled into the jacket of the fiber as opposed to the fiber core. For the same reason it proved necessary to place the PMT detector after the splice connector, which absorbs effectively light that travels through the jacket. To our surprise it was not necessary to remove the clear acrylate jacket or the cladding of the fiber in either the input or output region. A laser shot would typically result in the detection of 5 to 50 photons.

A 300 MHz 8 bit oscilloscope sampled the PMT signal output and this oscilloscope trace was transferred to a PC for storage, averaging, and analysis. The oscilloscope waveforms were averaged for up to 8,000 laser shots. The peaks from each roundtrip were integrated and their intensity decay was fitted to a bi-exponential decay.

These two decays correspond to light coupled into the cladding and into the fiber core. We have verified that the light coupled into the cladding can be (somewhat effectively) absorbed by removing the clear acrylate jacket and painting the cladding surface black. The evanescent wave of the light in the cladding will be absorbed and the overall intensity decreases.

From the ring-down times the dB loss and percent loss were calculated for both the slow and the fast decay process. The analysis also yielded the average distance between the peaks from which the average refractive index of the fiber can be easily determined by using the known length of the fiber loop. These measurements can be made very accurately using the ring-down trace (e.g., FIG. 2, for a 12 m loop).

Each of the roundtrips appears as a doubled peak in the ring-down trace. This is due to an artifact in our signal processing, as has been confirmed by recording the signal of a single photon, which also yields two signals spaced by about 4 ns.

Results

Figure 4:
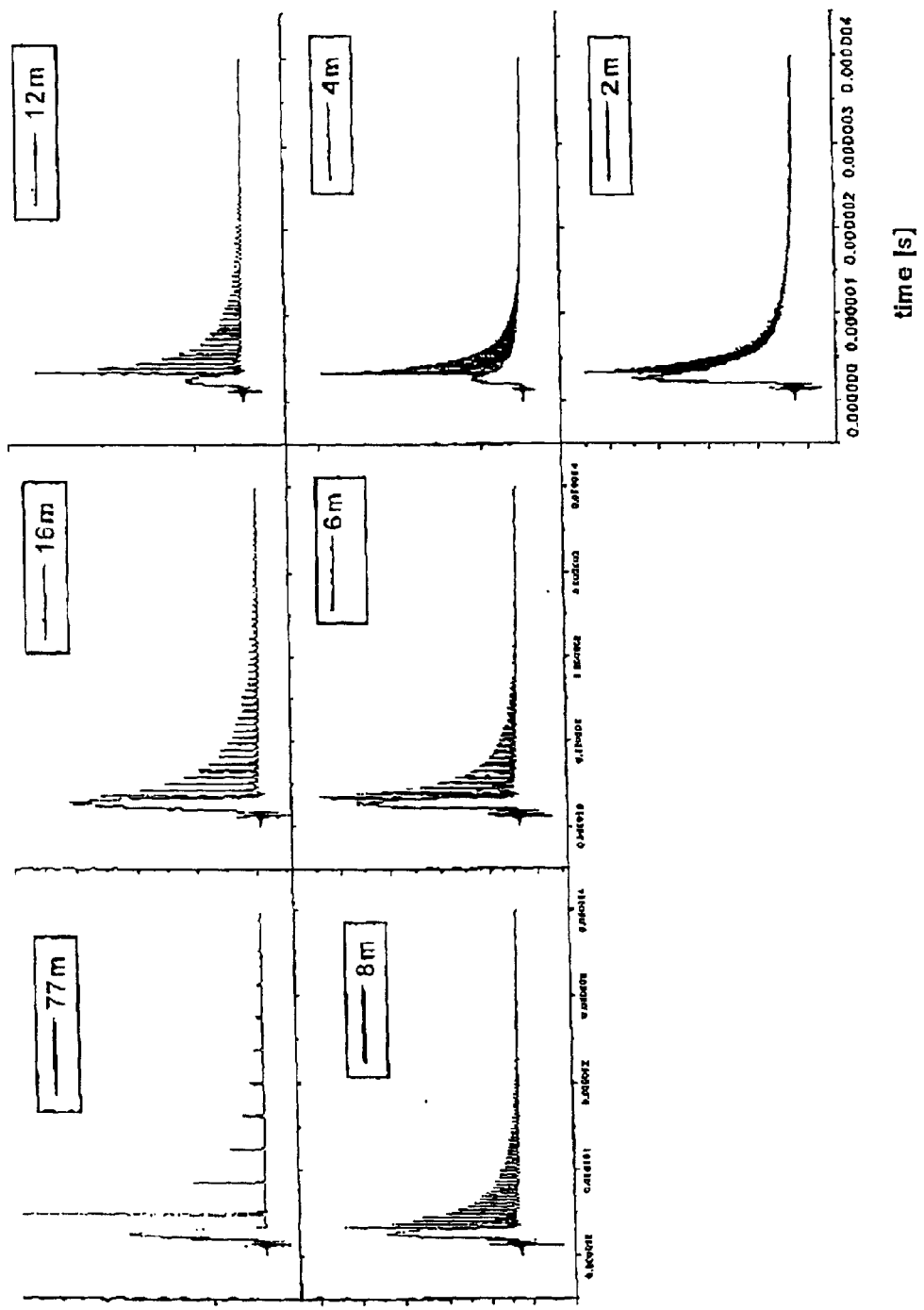
FIG. 4 shows ring-down traces recorded for different lengths of optical fiber joined with a single splice connector.
Figure 5:
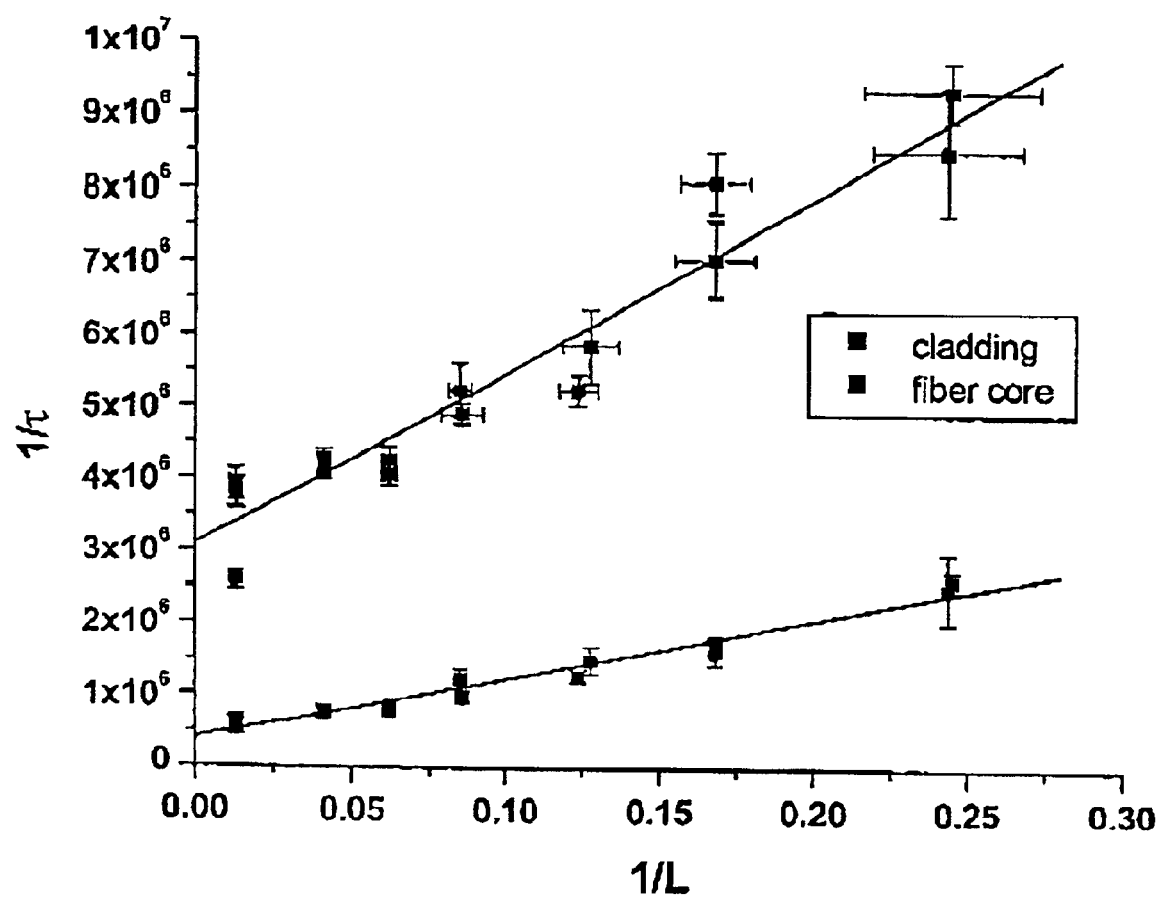
FIG. 5 shows a linear fit to a plot of the inverse of ring-down time as a function of the inverse of fiber length. The upper plot corresponds to the fast decay in the cladding material and the lower plot corresponds to the decay in the fiber core. From this plot the loss in the fiber and in the splice can be calculated for both fast and slow decay.

Shown in FIG. 4 are ring-down traces obtained with different lengths of fiber. It is apparent that the ring-down times are similar regardless of the length of the fiber, indicating that the optical loss occurs to a similar extent in the fiber itself and in the splice connector. The slight decrease in ring-down time permits the separation of the loss in the medium from the loss in the splice. From a linear fit of the inverse of the fiber length vs. the inverse of the ring-down time one can determine a) the loss in the fiber from the intercept and b) the loss in the splice from the slope. This fit is displayed in FIG. 5. Of course, since not all splices have identical characteristics there exists a distribution of the dB loss per splice, which may be determined using a larger number of the splices. From two trials it was found that the linear fit yields a loss of 4% (0.17 dB) (trial 2: 4.46% (0.20 dB)) in the splice for the slow decay process and 11% (0.53 dB) (trial 2: 13.3% (0.62 dB)) for the fast decay process, reflecting the better coupling of the fiber core butt ends in the splice as opposed to the coupling of the cladding. The loss of 0.17 or 0.20 dB in the splice for the 810 nm light in the fiber is considerably higher than the splice manufacturer's specification of 0.07 dB for 1300 nm light. The difference may be explained by the fact that the index matching fluid contained in the splice will contribute to loss processes should it absorb even slightly at 800 nm. The loss in the fiber material is similar for the two processes: It corresponds to 0.2% (trial 2: 0.092% (0.004 dB)) loss per meter of intensity in the fiber core and 1.5% (trial 2: 0.10% (0.043 dB)) in the cladding. The first pair of numbers compares well to the manufacturer's specifications of 0.1% loss in the fiber at around 800 nm.

Using this information one can estimate the total number of photons in the fiber core at any given time. Here we consider that each photon results in a 30 mV signal. One can then calculate that five photons would have been detected from the very first pulse by extrapolation of the slow decay trace to $t_0$. Considering that only 1 cm of the fiber is probed and the loss is 0.1%/m the total number of photons in the fiber core can be estimated as 500,000.

Figure 6:
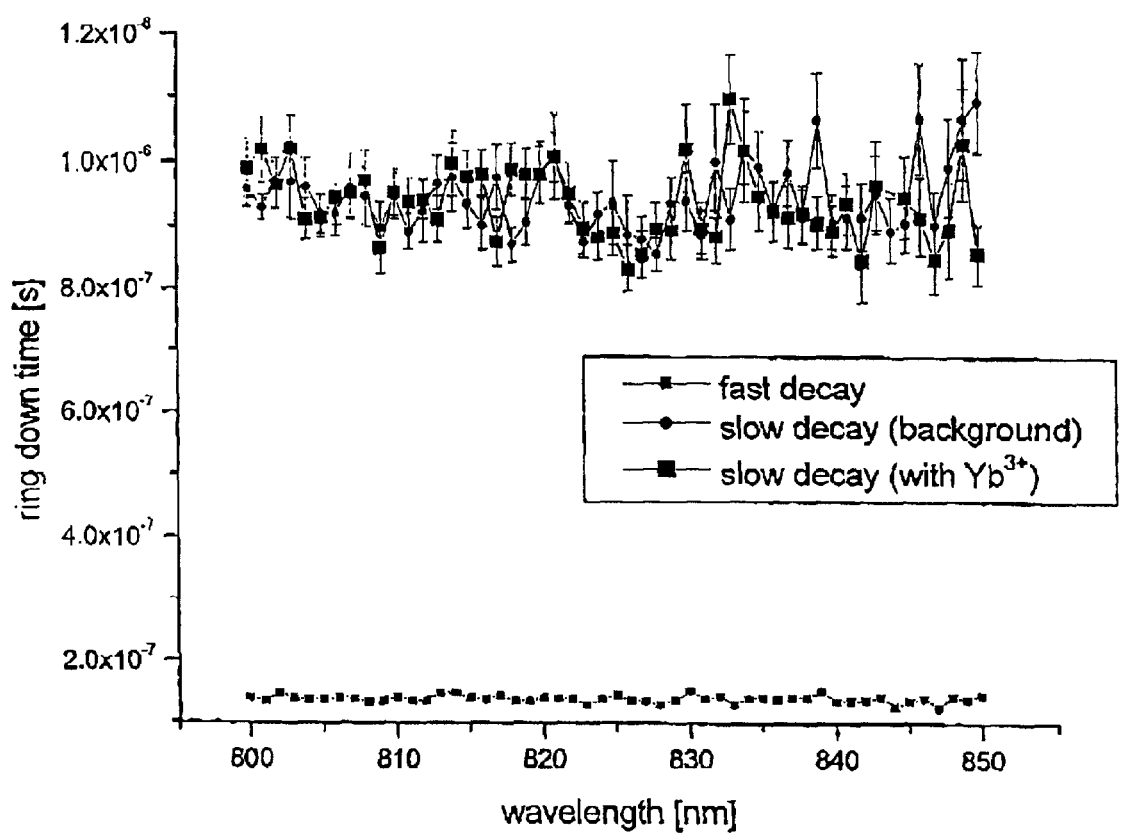
FIG. 6 is a plot of the spectrum of a fiber at 800 to 850 nm, which shows that there are no cavity resonances in either the entire loop or the cavity formed by the fiber end facets.

The spectrum of the fiber at around 800 nm to 850 nm (FIG. 6) shows no indication of the "cavity resonance" effects that are characteristic for the analogous experiments using a cavity defined by two highly reflective mirrors. The reasons for the absence of this effect are the broad 2 nm linewidth of the pulsed laser and the effective "scrambling"

of most modes in the 50 μm multimode fiber. As a consequence, the modes in our fiber form a quasi-continuum and a structureless transmission spectrum.

Example 2

A Ring-Down Absorption Detector for a Laboratory-on-a-Chip Device

Introduction

Recent developments in the area of micro-Total Analysis Systems (μ-TAS) have included systems that perform chemical reactions, separation and detection on a single microchip (Harrison et al. 1993; van den Berg et al. 2000). Compared to conventional systems, lab-on-a-chip devices have reduced analysis times and use minute amounts of sample, solvents and reagents due to their small dimensions. In fact, the analysis of a simple mixture has been performed in less than one millisecond using only 100 picoliters of sample (Jacobson et al. 1998). The small amounts of sample and reagent required, combined with rapid analyses, make microfluidic devices extremely attractive for several analytical applications including chemical analysis of biological and medicinal samples.

Currently, most microfluidic analyses utilize molecular fluorescence as a means of detection. However, fluorescence is not a universal method of detection because it requires the analyte of interest to be fluorescent. Since most analytes are not naturally fluorescent, complicated labeling protocols are often required to be make analytes amenable to this method of detection. Conversely, molecular absorption is a much more universal method of detection in analytical systems as evidenced by its widespread use in techniques such as liquid chromatography. However, absorption detection in a microchip has so far remained underutilized, primarily due to the short path length (microns) associated with the microfluidic channels, limiting detector sensitivity.

It is expected that the ring-down method of the invention will provide the sensitivity required for a microfluidic absorption spectroscopic technique for liquid samples with very short path lengths.

Absorbance Detection on a Microchip

Figure 7:
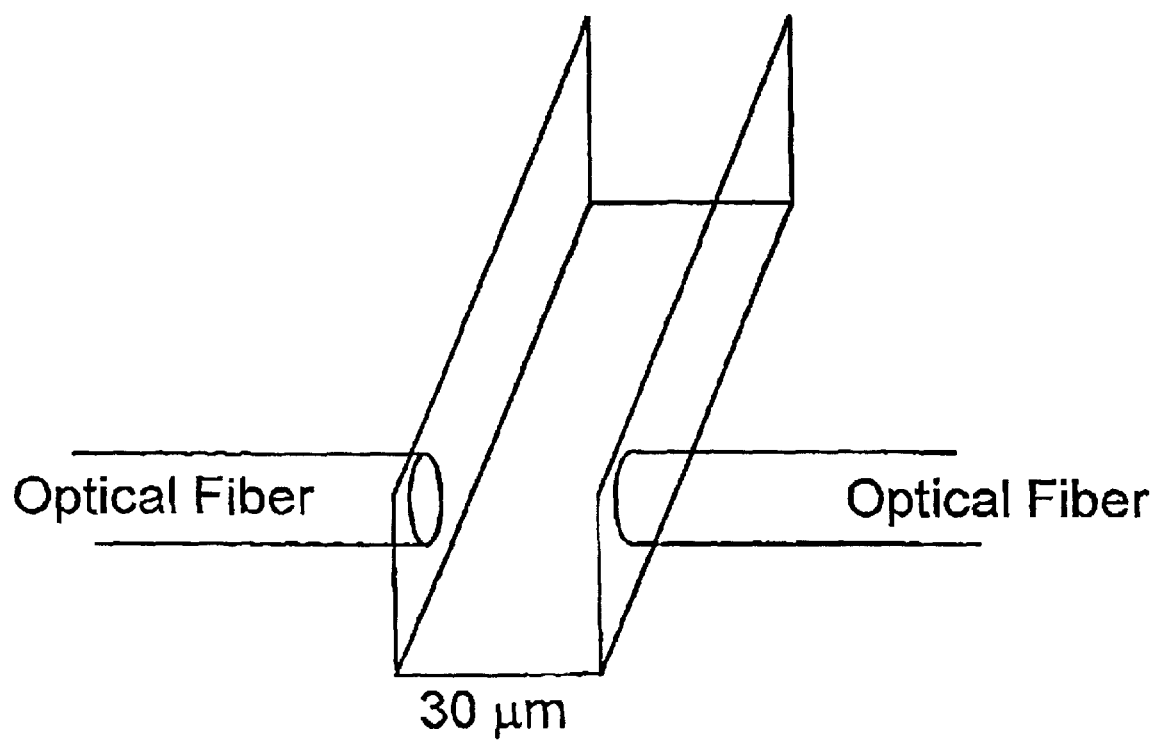
FIG. 7 is a schematic showing alignment of optical fibers on either side of a separation channel of a microfluidic absorbance detection chip.
Figure 8:
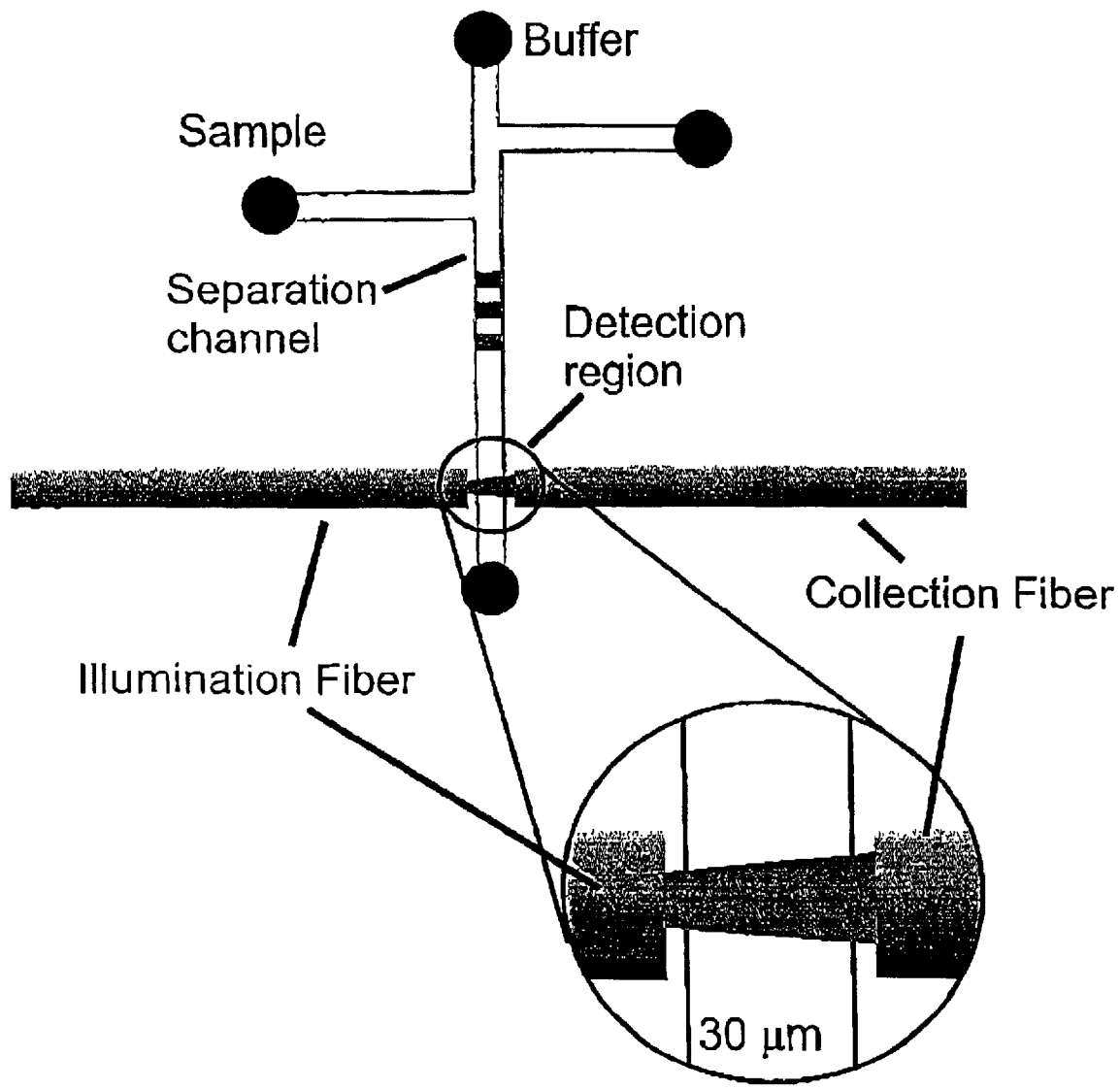
FIG. 8 is a schematic diagram of a polymeric lab-on-a-chip absorbance detection.

In conventional liquid chromatography, absorbance detection is often achieved using a flow cell. In microfluidic devices, the fluid channel diameter is roughly 1000 times smaller than conventional liquid chromatographic systems. The detection method must therefore be extremely sensitive, which relates in part on the alignment of focusing and collection optics. This can be achieved by using optical fibers to direct and collect the light transmitted through the small (e.g., 30 μg/m) sample channel (shown schematically in FIG. 7). Such devices can be made using polymeric materials, or conventional materials such as glass. Polymeric chips are preferred because of their low cost, and because they eliminate the necessity for complex machining and the need for photolithography, both of which are required when conventional materials are used. A polymeric microchip has optical waveguide cast directly within the polymer material, avoiding complex alignment of the fibers (FIG. 8). A suitable material is polydimethylsiloxane (PDMS), into which structures as small as 10 nanometers can be cast, and which is relatively easy to use. Once a micro-fabricated mold has been produced, polymeric devices can be rapidly fabricated using a micro-molding procedure.

For conventional materials, commercially available glass microchip devices from Micralyne Inc. (Edmonton, AB) are suitable and can be modified to accept the optical fibers. Modification involves the precise positioning of optical fibers across the fluidic channel. For example, to facilitate the fiber optic coupling, small receiving sleeves can be drilled (using micro-drill bits, 180 μm dia. and a high precision drill) on either side of the microfluidic channel. Care must be taken as to the precise depth of sleeves (too shallow, poor light collection efficiency; too deep, fluidic channel will be disrupted). Optical fibers can be placed in the sleeves aligned and anchored into place with a reversible sealant. Fiber alignment involves filling the absorbance cell with a fluorescent dye and examining the path of light through the flow channel. Index matching fluid can be used in the sleeves to increase light coupling efficiency. Once mated with optical fibers, the microchip is coupled to illumination/detection equipment as shown in FIG. 8. Alternatively, one can select the fiber diameter to be much larger than the capillary through which the analyte is delivered. The sample is then inserted directly into a hole in the optical fiber, thereby inducing minimum alignment losses.

Figure 9:
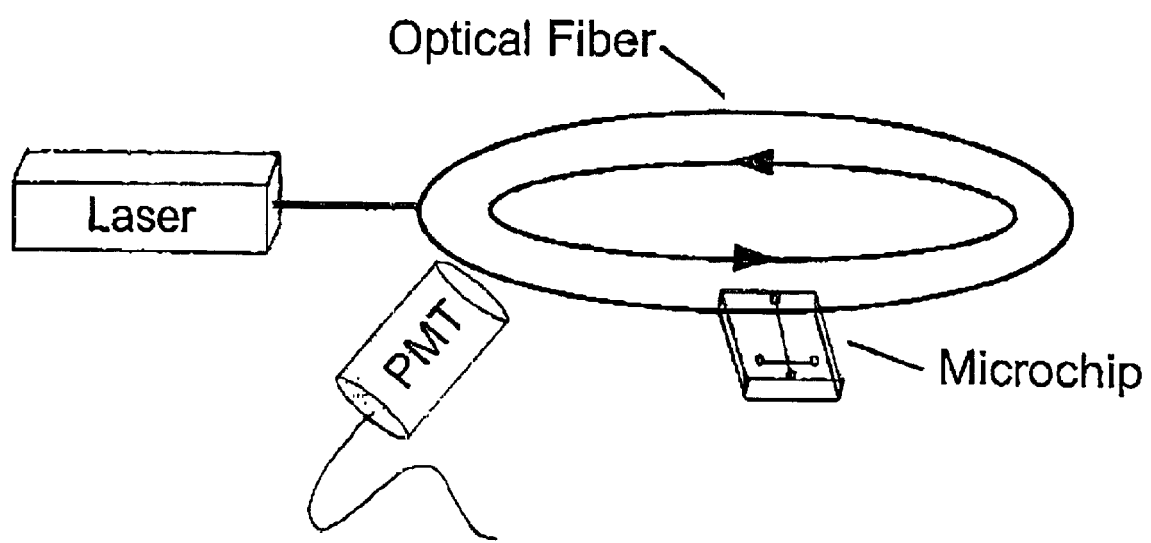
FIG. 9 is a schematic diagram of a microfluidic absorption cell with a fiber loop ring-down detection system.

As can be seen in FIG. 9, a polymeric or conventional microchip, used in either of the two configurations above, is inserted into an optical loop with a pulsed light source. A pulse of light from the light source travels around the loop until all the light has been absorbed by the sample and/or lost through absorption or scattering within the optical fiber. As the light pulse travels around the loop it repeatedly passes through the flow cell and encounters the sample flowing through the flow cell. The sample flowing through the flow cell will be "sampled" many times increasing the "effective" path length of the detector. The circulating pulse is monitored by a photomultiplier tube (PMT) that detects stray light from the pulse as it passes through the fiber in front of the PMT. For each laser pulse a sequence of exponentially decaying ring-down pulses ("roundtrips") is observed. The loss can be described by the 1/e ring-down time, as shown in Example 1.

The ring-down time characterizes a single exponential decay of the amplitude of the roundtrips and depends on the loss in the sample and inside the fiber. As is apparent from the above equation, in the calculation of the transmissivity one will have to distinguish between losses that occur once per roundtrip and processes that occur continuously. Most importantly, since the observable is the "ring-down time", the absorbance measurement is independent of the amplitude of the laser pulses coupled into the fiber and therefore the measurement is not sensitive to shot-to-shot noise of the pulsed laser, to input coupling efficiency, or to drift of the laser power with time or wavelength.

In addition, the sensitivity of the detection scheme provided herein is expected to be several fold greater than that provided by conventional techniques. The sensitivity of the system can be quantified, for example, by measuring absorbance of various concentrations of organic dye with high molar extinction coefficients. For example, a solution of a strongly absorbing compound passed through the channel will produce a decrease in light intensity, which can be monitored to determine the sensitivity of the absorption cell. The sensitivity of the device, in terms of its ability to detect and resolve closely-spaced chromatographic peaks, can be examined through measurement of, for example, an electrophoretic separation of different rhodamine dyes.

Example 3

A Ring-Down Absorption Detector

An experimental setup as shown in FIG. 1 was used. The light source was a nitrogen (or Nd:YAG) laser-pumped dye laser with a bandwidth of about 2 nm, a pulse width of 500 ps (or 7 ns) and a power of 50–200 μJ. The mildly focussed output of this laser was coupled into an optical fiber loop (length 1 m–77 m) at a 3 cm radius bend of the fiber (multimode Anhydroguide-G LOW OH Vis-IR Fiber, Fiberguide Industries, 50 µm core, 125 µm cladding). The loop was completed using a splice connector (Fibrlok®, 3M). A photomultiplier tube (PMT) (Hamamatsu, R955) was located at a distance (minimum=50 cm) away from the excitation region and monitored the emitted light at a similar 3 cm radius bend of the fiber. The PMT was gated such that the first 270 ns after each laser pulse were not recorded. This was done because the initial photon signal had abnormally high intensity, probably resulting from stray light and light coupled into the jacket of the fiber as opposed to the fiber core. For the same reason the PMT detector was placed after the splice connector, which absorbs effectively light that travels through the jacket. However, it was not necessary to remove the clear acrylate jacket or the cladding of the fiber in either the input or output region. A laser shot would typically result in the detection of about 50 to 200 photons.

A 300 MHz 8 bit oscilloscope sampled the PMT signal output and this oscilloscope trace was transferred to a PC for storage, averaging and analysis. The oscilloscope waveforms were averaged for 3,000 to 10,000 laser shots depending on the laser wavelength and the sensitivity of the PMT detector at this wavelength. The peaks from each roundtrip were integrated and their intensity decay was fitted to a bi-exponential decay with significantly different decay times. These two decays correspond to light coupled into the cladding and into the fiber core.

Ring-down times were calculated as described in Example 1, above. From the ring-down times the dB loss and percent loss were calculated for both the slow and the fast decay process. The analysis also yielded the average distance between the peaks from which the average refractive index of the fiber can be easily determined using the known length of the fiber loop.

To test the capabilities of the fiber-loop ring-down technique as an absorption technique for microcavities, the index matching fluid in the fiber splice was replaced with a solution of 1,1'-diethyl-4,4'-dicarbocyanide iodide (DDCI-4) in dimethyl-sulfoxide (DMSO) and the ring-down time at 825 nm was measured as a function of concentration (FIG. 4). The dye was selected because of its comparably narrow absorption spectrum in a wavelength range at which the PMT detector operates well and the transmission of the fiber is acceptable. The solvent was selected for its low vapour pressure and low absorption in this wavelength range.

The ring-down time now contains an additional term due to the adjustable absorption inside the splice:

$$\tau = \frac{L}{c_0[\varepsilon_{DDCI}c_{DDCI}l + \varepsilon_{DMSO}l - \ln T_{splice} + \varepsilon_{Fiber}L]}$$

Figure 10:
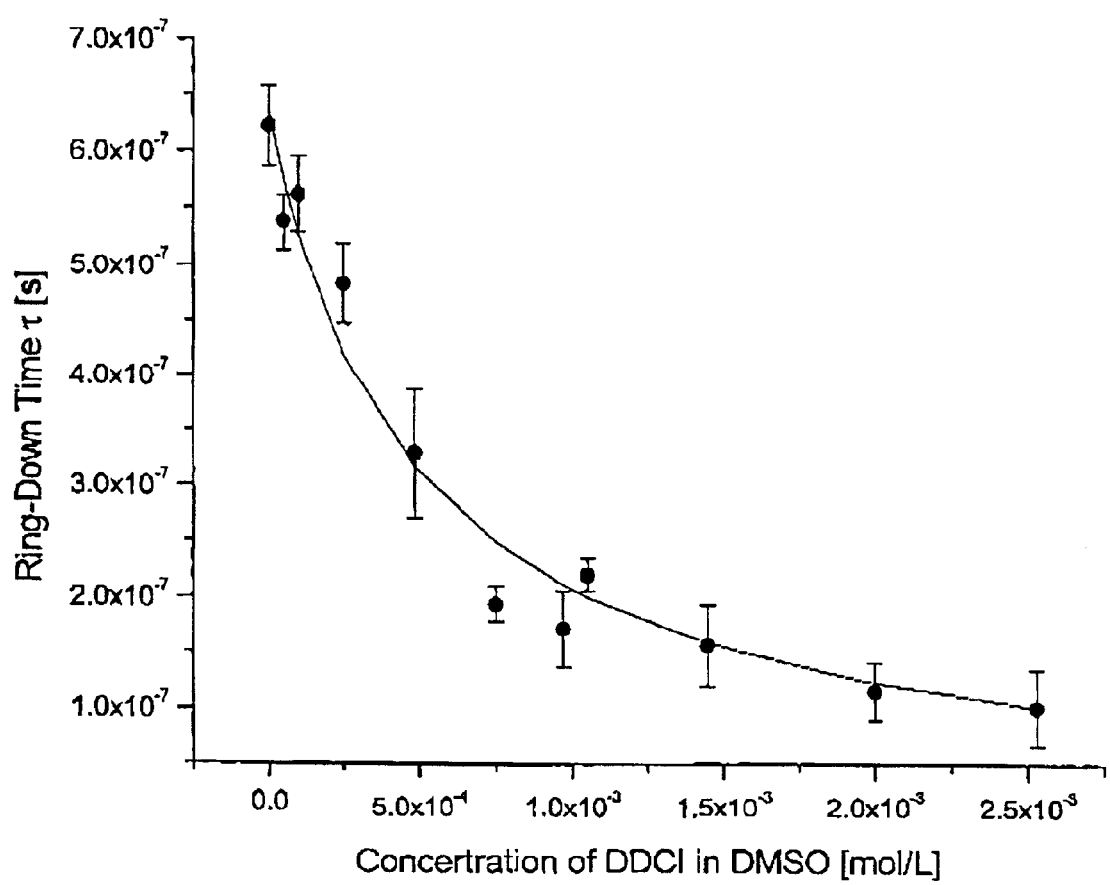
FIG. 10 is a plot of ring-down time as a function of concentration of DDCI. The uncertainties indicated in the plot are curve-fitting errors and do not include errors due to differences of the splices used. The solid line indicates the fit from which the average path length inside the splice was calculated as 3.8 $\mu$m.

Here $\varepsilon_{DDCI}$ is the extinction coefficient of DDCI-4 at its peak absorption wavelength of 825 nm, $C_{DDCI}$ is its concentration, and l is the width of the cavity formed by the two fiber ends. The term $\varepsilon_{DMSO}$ is introduced to attribute for the absorption of the solvent. From a comparison with the ring-down time without DDCI and the independently obtained extinction coefficient of DDCI, it was possible to characterize the size of the cavity formed between the two fiber ends. The cavity corresponds to a cylindrical cavity of 50 µm diameter and 3.5 µm width and hence to a total volume of about $7 \times 10^{-12}$ L. From FIG. 10 it can be seen that, for example, a 100 µMol change in concentration of DDCI in the sample leads to a substantial change in the ring-down time and can readily be detected. Therefore, the absorption technique of the invention provides a detection limit for DDCI of about $7 \times 10^{-16}$ mol, i.e., $3.5 \times 10^{-13}$ g. It is expected that the absorption technique of the invention will yield similar results with other compounds of interest.

Figure 11:
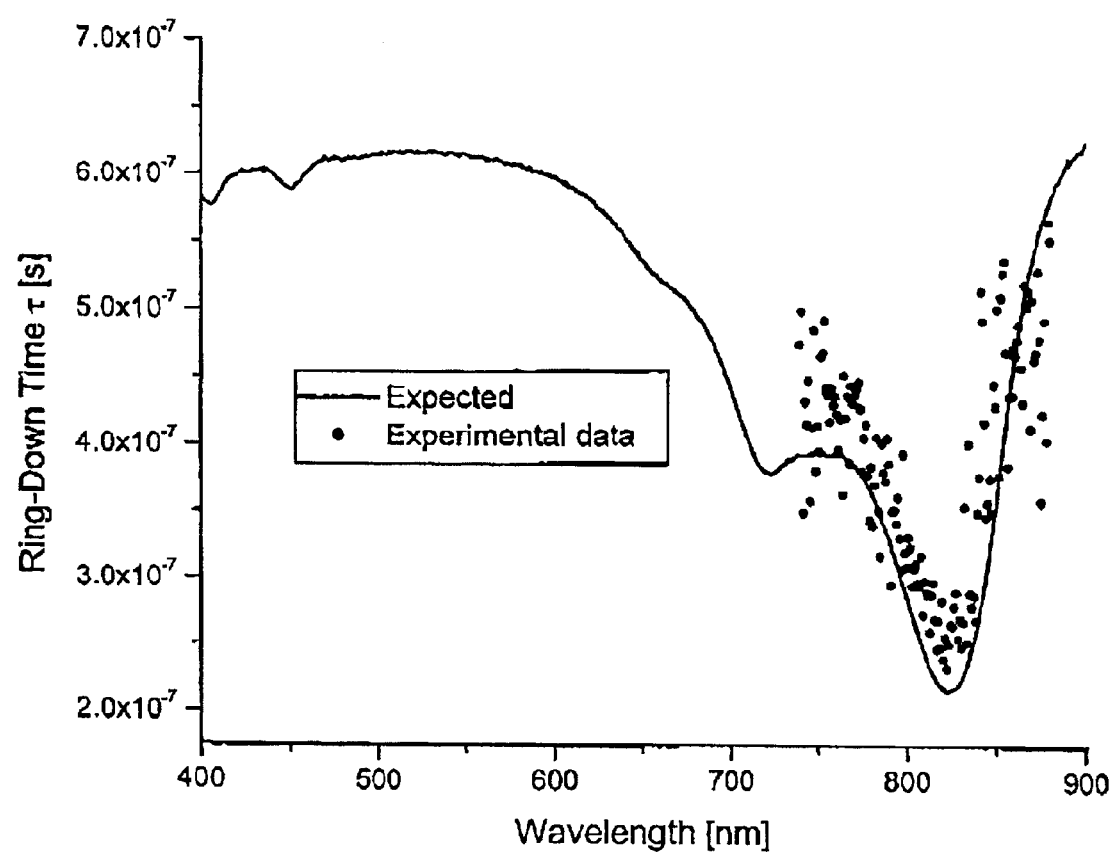
FIG. 11 is a plot of the absorption spectrum of DDCI at around 800 nm showing the experimental ring-down times compared to the theoretical curve (solid line) modelled assuming a 4 $\mu$m gap between the fiber ends.

To further examine the capabilities of the fiber-loop ring-down absorption technique, an absorption spectrum of DDCI in DMSO was recorded over the range of 740 nm–880 nm. Using the above equation and an absorption spectrum in a 10 mm cuvette, we calculated the expected variation in ring-down times as a function of excitation wavelength. FIG. 11 shows a comparison between the expected wavelength dependence of ring-down times and the experimental data. The size of the cavity was assumed to be characterized by the 50 µm diameter of the fiber and a 3.5 µm spacing between the ends of the fiber. As can be seen from FIG. 11, good agreement was obtained.

The spectrum of the fiber (FIG. 11) shows no indication of the "cavity resonance" effect that is characteristic for experiments using a cavity defined by two highly reflective mirrors. Two reasons for the absence of this effect are the broad 0.04 nm bandwidth of the pulsed laser and the effective "scrambling" of modes in the 50 µm core multimode fiber. As a consequence, the modes in our fiber form a quasi-continuum and a feature-less transmission spectrum over the tuning range.

The length of the fiber loop was chosen such that the signals from each roundtrip were well separated, but there is no reason why one could not use laser pulses of greater pulse width and/or shorter optical waveguide loops and measure the envelope of the ring-down signal as opposed to the integral of the individual roundtrips. This would likely improve the quality of the fit since a larger number of points would be available to describe the exponential decay. We note that in contrast to most other absorption techniques, the number of data points available for extraction of the absorption signal is in fact larger for weak absorption processes than for strong absorption processes. Therefore, the technique is expected to perform well for weak absorbers and/or short absorption path lengths.

In an alternative embodiment, the apparatus can be simplified by replacing the laser source with a fast LED that illuminates a fiber loop wrapped not only once but many times around a cylinder. Different parts of the fiber loop would then simultaneously be illuminated and read out. The ring-down signal would not carry a signature of separate pulses, but would consist of a smooth exponential decay.

From the above it can be seen that the ring-down absorption technique of the invention can be applied to a laboratory-on-a-chip device, such as a microfluidic device, as described in Example 2, above. Such implementation essentially involves the substitution of the splice connector of the present example with a microfluidic device as described in Example 2.

Those skilled in the art will recognize, or be able to ascertain using routine experimentation, variations of the embodiments and examples described herein. Such variations are intended to be within the scope of the invention and are covered by the appended claims.

REFERENCES

Berden, G., R. Peeters, and G. Meijer, 2000, Cavity ringdown spectroscopy: Experimental schemes and applications, *International Reviews in Physical Chemistry* 19:565–607.

Engeln, R., von Helden, G., van Roij, A. J. A., and Meijer, G., 1999, *J. Chem. Phys.* 110:2732.

Eiselt, M., W. Pieper, G. Grosskopf, R. Ludwig, and H. G. Weber, 1993, One Million Pulse Circulations in a Fiber Ring Using SLALOM for Pulse Shaping and Noise Reduction, *IEEE Photonics Technology Letters* 4:422.

Hallock, A. J., Berman, E. S. F., Zare, R. N., 2002, *Anal. Chem.* 74:1741.

Harrison, D. J., K. Fluri, K. Seiler, Z. Fan, C. S. Effenhauser, A. Manz, 1993, *Science* 261:895–897.

Jacobson, S. C., C. T. Culbertson, J. E. Daler, J. M. Ramsey, 1998, *Anal. Chem.* 70:3476–3480.

Langenhorst, R., M. Eiselt, W. Pieper, G. Grosskopf, R. Ludwig, L. Kuller, E. Dietrich, and H. G. Weber, 1996, Fiber loop optical buffer, *Journal of Lightwave Technology* 14:324–335.

*Optical Fiber Sensors: Systems and Applications*, Vol. 2, Artech House, Inc., Norwood, 1989.

Pipino, A. C. R., J. W. Hudgens, and R. E. Huie, 1997, Evanescent wave cavity ring-down spectroscopy with a total-internal-reflection minicavity, *Review of Scientific Instruments* 68:2978–2989.

Romanini, D. and K. K. Lehmann, 1993, Ring-down cavity absorption spectroscopy of the very weak HCN overtone bands with six, seven, and eight stretching quanta, *J. Chem. Phys.* 99:6287.

Scherer, J. J., J. B. P. O'Keefe, and R. J. Saykally, 1997, Cavity ring-down laser absorption spectroscopy: History, development, and application to pulsed molecular beams, *Chemical Reviews* 97:25.

Stewart, G., Atherton, K., Yu, H., Culshaw, B., 2001, 2001, *Meas. Sci. Technol.* 12:843.

van den Berg, A., W. Olthuis and P. Bergveld, Kluwer, 2000, *Micro Total Analysis Systems* 2000, *Proceedings of the µTAS 2000 Symposium.* von Lerber, T., Sigrist, M. W., 2002, *Chem. Phys. Lett.* 353:131.

Xu, S., Sha, G., Xie, J., 2002, *Rev. Sci. Instr.* 73:255.

Yamanaka, Y., T. Numai, K. Kasahara, and K. Kubota, 1993, Optical Fiber Loop Memory using Vertical to Surface Transmission Electro-Photonic Devices, *Journal of Lightwave Technology* 11:2140.

We claim:

1. A method for measuring one or more optical properties of a test medium, comprising:
   providing an optical waveguide loop comprising a test medium;
   illuminating the optical waveguide loop with a plurality of light pulses; and
   detecting roundtrips of said light pulses at one or more locations along the loop;
   wherein said detected light pulses are indicative of one or more optical properties of the test medium.

2. The method of claim 1, further comprising determining ring-down time of said light pulses.

3. The method of claim 2, wherein a period between light pulses is greater than the ring-down time of a light pulse.

4. The method of claim 3, wherein the ring-down time is determined from the sum of ring-down waveforms for the light pulses.

5. The method of claim 3, wherein said light pulses have a pulse width shorter than the roundtrip time of a light pulse, such that roundtrips from each light pulse are separated in time.

6. The method of claim 3, wherein said light pulses have a pulse width greater than the roundtrip time of a light pulse, such that an envelope of the ring-down signal is measured.

7. The method of claim 2, wherein a period between light pulses is less than the ring-down time of a light pulse.

8. The method of claim 7, wherein the ring-down time is determined from the sum of ring-down waveforms for the light pulses.

9. The method of claim 7, wherein said light pulses have a pulse width shorter than the roundtrip time of a light pulse, such that roundtrips from each light pulse are separated in time.

10. The method of claim 7, wherein said light pulses have a pulse width greater than the roundtrip time of a light pulse, such that an envelope of the ring-down signal is measured.

11. The method of claim 1, wherein the optical waveguide loop is passive.

12. The method of claim 1, wherein the optical waveguide is an optical fiber.

13. The method of claim 12, wherein the optical waveguide further comprises a fiber optic splice connector.

14. The method of claim 12, wherein the optical waveguide further comprises a fusion spliced connection.

15. The method of claim 1, wherein the waveguide loop is the test medium.

16. The method of claim 1, further comprising:
   providing a channel for intercepting light that is guided by the optical waveguide loop; and
   disposing the test medium in the channel;
   wherein the test medium in the channel is exposed to said light.

17. The method of claim 1, wherein the test medium is in the vicinity of the optical waveguide loop and is exposed an evanescent wave of light that is guided by the optical waveguide loop.

18. The method of claim 1, wherein the optical property is absorbance.

19. The method of claim 1, wherein the optical property is refractive index.

20. The method of claim 1, wherein the light pulses have at least one wavelength selected from infra-red (IR), visible, and ultra-violet.

21. The method of claim 1, the number of light pulses is between about 10 and 10,000.

22. The method of claim 1, wherein the test medium is selected from a gas, a liquid, and a solid material.

23. A method for measuring one or more optical properties of a test medium, comprising:
   providing an optical waveguide loop comprising a test medium; and
   measuring ring-down time of a plurality of light pulses travelling around the loop and through the test medium;
   wherein the ring-down time is indicative of one or more optical properties of the test medium.

24. The method of claim 23, wherein the optical waveguide loop is passive.

25. An apparatus for measuring one or more optical properties of a test medium, comprising:
   an optical waveguide loop comprising a test medium;
   a light source for illuminating the loop with a plurality of light pulses; and
   a detector for detecting roundtrips of said light pulses at one or more locations along the loop;
   wherein said detected light pulses are indicative of one or more optical properties of the test medium.

26. The apparatus of claim 25, further comprising a device for displaying and/or storing and/or manipulating data corresponding to light pulses.

27. The apparatus of claim 25, wherein ring-down time of said light pulses is determined from said detected light pulses.

28. The apparatus of claim 27, wherein a period between light pulses is greater than the ring-down time of a light pulse.

29. The apparatus of claim 28, wherein the ring-down time is determined from the sum of ring-down waveforms for the light pulses.

30. The apparatus of claim 28, wherein said light pulses have a pulse width shorter than the roundtrip time of a light pulse, such that roundtrips from each light pulse are separated in time.

31. The apparatus of claim 28, wherein said light pulses have a light pulse width greater than the roundtrip time of a light pulse, such that an envelope of the ring-down signal is measured.

32. The apparatus of claim 27, wherein a period between light pulses is less than the ring-down time of a light pulse.

33. The apparatus of claim 32, wherein the ring-down time is determined from the sum of ring-down waveforms for the light pulses.

34. The apparatus of claim 32, wherein said light pulses have a pulse width shorter than the roundtrip time of a light pulse, such that roundtrips from each light pulse are separated in time.

35. The apparatus of claim 32, wherein said light pulses have a pulse width greater than the roundtrip time of a light pulse, such that an envelope of the ring-down signal is measured.

36. The apparatus of claim 32, wherein the optical waveguide further comprises a fusion spliced connection.

37. The apparatus of claim 25, wherein the optical waveguide loop is passive.

38. The apparatus of claim 25, wherein the optical waveguide is an optical fiber.

39. The apparatus of claim 38, wherein the optical waveguide further comprises a fiber optic splice connector.

40. The apparatus of claim 25, wherein the waveguide loop is the test medium.

41. The apparatus of claim 25, further comprising:
a channel into which the test medium is disposed, the channel intercepting light that is guided by the optical waveguide loop;
such that the test medium in the channel is exposed to said light.

42. The apparatus of claim 41, wherein the apparatus comprises a microfluidic device.

43. The apparatus of claim 25, wherein the test medium is in the vicinity of the optical waveguide loop and is exposed an evanescent wave of light that is guided by the optical waveguide loop.

44. The apparatus of claim 25, wherein the optical property is absorbance.

45. The apparatus of claim 25, wherein the optical property is refractive index.

46. The apparatus of claim 25, wherein the light pulses have at least one wavelength selected from infra-red (IR), visible, and ultra-violet.

47. The apparatus of claim 25, wherein the number of light pulses is between about 10 and 10,000.

48. The apparatus of claim 25, wherein the test medium is selected from a gas, a liquid, and a solid material.

49. An apparatus for measuring one or more optical properties of a test medium, comprising:
an optical waveguide loop comprising a test medium;
a light source for illuminating the loop with a plurality of light pulses;
a detector for detecting roundtrips of said light pulses at one or more locations along the loop; and
a device for displaying and/or storing and/or manipulating data corresponding to light pulses;
wherein ring-down time of said light pulses is determined; and
wherein said ring-down time is indicative of one or more optical properties of the test medium.

50. The apparatus of claim 49, wherein the optical waveguide loop is passive.

* * * * *